United States Patent
Pozzato

(10) Patent No.: US 7,300,437 B2
(45) Date of Patent: Nov. 27, 2007

(54) ELECTRONIC SCALPEL TO CUT ORGANIC TISSUES

(75) Inventor: Gianantonio Pozzato, Vicenza (IT)

(73) Assignee: Telea Electronic Engineering SRL, Quinto Vicento (IT)

( * ) Notice: Subject to any disclaimer, the term of this patent is extended or adjusted under 35 U.S.C. 154(b) by 0 days.

(21) Appl. No.: 10/559,281

(22) PCT Filed: Jun. 3, 2004

(86) PCT No.: PCT/EP2004/051018

§ 371 (c)(1),
(2), (4) Date: Dec. 2, 2005

(87) PCT Pub. No.: WO2004/108000

PCT Pub. Date: Dec. 16, 2004

(65) Prior Publication Data

US 2006/0167447 A1    Jul. 27, 2006

(30) Foreign Application Priority Data

Jun. 6, 2003   (IT) .......................... VI2003A0110

(51) Int. Cl.
*A61B 18/18* (2006.01)

(52) U.S. Cl. ................ 606/39; 606/34; 606/41; 606/42; 606/45; 606/48; 128/898

(58) Field of Classification Search ................ 606/34, 606/39–42, 45, 48–50
See application file for complete search history.

(56) References Cited

U.S. PATENT DOCUMENTS

| 4,114,623 A | 9/1978 | Meinke et al. | |
|---|---|---|---|
| 5,971,980 A * | 10/1999 | Sherman | 606/34 |
| 6,458,122 B1 * | 10/2002 | Pozzato | 606/37 |
| 6,679,269 B2 * | 1/2004 | Swanson | 128/898 |

FOREIGN PATENT DOCUMENTS

| DE | 3904558 | 8/1990 |
|---|---|---|
| DE | 200 14 128 | 4/2001 |
| WO | WO 99/65411 | 12/1999 |
| WO | WO 02/053048 | 7/2002 |

* cited by examiner

*Primary Examiner*—Linda C. M. Dvorak
*Assistant Examiner*—Jacqueline Papapietro

(57) ABSTRACT

The electrode of a manipulator cuts tissue. The scalpel has rectifying circuit for supplying a rectified voltage to a radio frequency circuit which produces an output current signal at a substantially constant frequency to the electrode. The radio frequency circuit has an electronic switch controlled by an oscillator and pilot circuit. According to the method a wave form is applied to the electrode having such a power that the energy transferred to the manipulator is substantially equal to the sum of the energies required to break the bonds of the molecules of the tissue to be cut. The invention relates also to the electronic scalpel carrying out said method.

13 Claims, 2 Drawing Sheets

ELECTRONIC SCALPEL TO CUT ORGANIC TISSUES

BACKGROUND OF THE INVENTION

The present invention relates to an electronic scalpel to cut organic tissues, adapted for surgical applications.

More particularly, as it will be better pointed out hereinafter, the invention relates to an electronic scalpel adapted to transfer to the manipulator an electric power and therefore energy adapted to break the bonds of the molecules forming the organic tissue to be cut, without sensibly raising the temperature of the adjacent tissues.

European patent EP 1087691 discloses an electronic scalpel operating at a frequency of 4 MHz which is particularly adapted to avoid necrotic effects on the cells adjacent to the area to be cut.

The wave form available at the manipulator according to the disclosure of said patent, has no harmonics, as this wave signal derives from a radio frequency circuit closed on a resonant load essentially consisting of the eddy capacity of one or more MOSFETs and the inductance of the radio frequency transformer.

Tests effected on cuts made with such a kind of electronic scalpel still highlighted the presence of some necrotic cells around the cut due to cell heating.

Additional studies carried out highlighted that the cells undergoing the cutting operation, are not subject to necrotic degenerations when the energy transferred to break the molecular bond of these cells is substantially equal to the energy holding together said molecular bond.

As a matter of fact whenever energy is transferred to a cellular tissue, this causes the tissue molecules to vibrate and the increase of kinetic energy is transformed into a temperature increase of said tissue.

When temperature of the cells is raised to about 50° C. or more, the cells necrotize and die.

Therefore it is extremely important to operate in such a way that the electronic scalpel carries out the cutting operation without producing heat in the surrounding tissue.

As pointed out above, the phenomenon of temperature increase does not occur when and only when the energy transferred to the tissue molecules is equal to the molecule bonding energy.

Indeed in this case the delivered energy is not used to increase the molecule kinetic energy, but only to break the bond joining the molecules to each other.

On the other hand the molecules forming a kind of organic tissue on which the surgical cut should be effected are not all of the same nature and therefore some of them, even in a lower quantity, are characterized by having a bonding energy different from the molecules of the main tissue.

SUMMARY OF THE INVENTION

The main object of the invention is to propose a method of regulating a device transmitting the wave form to the manipulator of the electronic scalpel, and to provide such an electronic scalpel that transfers to the tissue an energy generally equally to the bonding energy of the different molecules of the tissue.

Consequently the purpose is to obtain that the molecules of the tissue undergoing the cutting operation are not subject to such a heating to compromise the functionality of the cells close to the cutting point.

Another object is to restrict as much as possible the bleeding phenomena connected with the tissue cutting operation.

A further object is to reduce as much as possible the oedematous tissue and the possibility of cheloid formation and post operative troubles.

The foregoing objects and others that will be better highlighted hereinafter, are attained by the electronic scalpel of the invention that according to the contents of the main claim is of the kind comprising:

- a manipulator to cut organic tissues;
- a rectifying circuit fed by the mains voltage to feed rectified and direct voltage to a radio frequency circuit;
- a radio frequency circuit comprising at least an electronic switch fed by said rectified and direct voltage and controlled by a pilot circuit emitting a generally square current wave of predetermined amplitude and frequency;
- at least an electrode in contact with the body having organic tissues to be cut, wherein said scalpel is characterized in that said circuit is a wide pass-band resonant circuit adapted to transfer to the manipulator a sinusoidal voltage distorted by the presence of a plurality of harmonics.

The invention concerns also the method of regulating the power available at the manipulator of an electronic scalpel of the above mentioned kind, characterized by applying to said manipulator a wave form having such a power that the energy due to the wave form of the resonant frequency and the harmonics transferred to the manipulator, is equal to the sum of the energies required to break the bonds of the molecules forming the tissue to be cut.

Advantageously according to the invention the presence at the manipulator of a plurality of harmonics belonging at least to the second and the third order even if dampened, results in a supply energy of a different quantity and quality in addition to the energy of the fundamental wave so that to the various kinds of molecules of the tissue to be cut. Accordingly energy is supplied which is equal to the bonding energy for each type of molecule.

It is clear that in this way, by supplying to each molecule its own bonding energy, the bond joining the molecules to each other is broken without causing molecule degradation due to heating and therefore avoiding that the tissue cells undergo a considerable heating.

As a matter of fact the cell temperature remains under 50° C. so that their functionality is kept unaltered.

The advantage arising from this absolute limitation of the molecular and therefore cellular heating involves a number of very interesting and unexpected benefits.

Indeed use of the electronic scalpel according to the invention, in addition to avoid necrosis of the cells adjacent to the cut, attains a very quick recovery, a tissue resuturation without problems, a patient's pain surprisingly under the normal pain threshold, a reduced bleeding and a dramatic reduction of all the post operative troubles.

Moreover no stimulation was observed when operations were effected close to nerves or nerve endings.

With this method of supplying only the bond energy of the tissue molecules to the cutting area and therefore to the tissue to be cut, it was observed that it is possible to obtain very quick biopsies of high quality because the taken samples are not damaged and consequently the analysis carried out are totally reliable.

The temperature of the tissue involved in the action carried out by the electronic scalpel of the present invention was always kept below 50° C. which is recognized to be the limit temperature under which the cells do not necrotize.

BRIEF DESCRIPTION OF THE DRAWINGS

Further characteristics and features of the invention will be better highlighted in the following description of a particular embodiment of the invention given as an illustrative but not limiting example and shown in the accompanying sheets of drawings in which.

DESCRIPTION OF THE INVENTION

Figure 1:
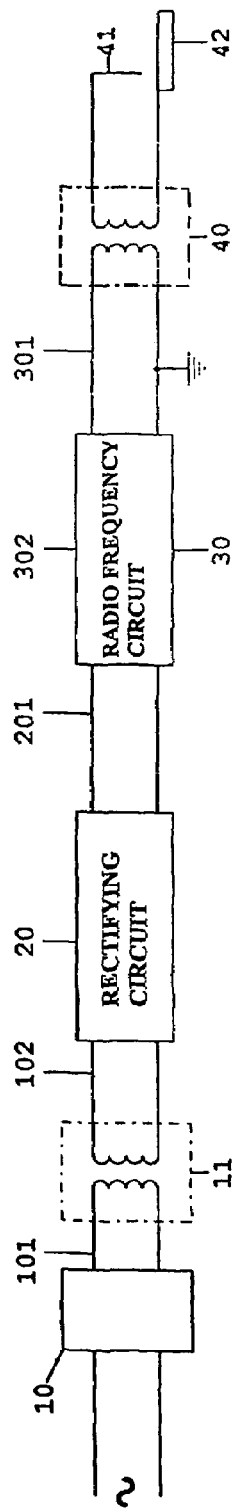
FIG. 1 is block diagram of the electronic scalpel of the invention.

With references now to the figures of the drawings and more particularly to FIG. 1, one can see that the circuit of the electronic scalpel is fed by the mains voltage and is provided with an input filter 10 as a protection against the possible radio frequency noise existing on the mains or that could enter the mains from the electronic scalpel.

The circuit is also provided with a transformer indicated with 11, whose input is a voltage 101 for instance of 230 V, and having a voltage output 102 reduced to about 140 or 160 V.

This voltage enters the rectifying circuit 20 which is a normal rectifying diode circuit with double half wave transforming the alternated current into a pulsating rectified current which is then filtered so that at the output there is a rather high direct voltage 201 for instance of 220 V, constituting the feed of the radio frequency circuit 30.

According to an executive embodiment of the invention, instead of the transformer 11 and the rectifying circuit with filter 20 a stabilized switching AC/DC converter can be used, or a transformer coupled with a rectifying circuit with filter having a stabilized switching DC/DC converter in output.

In any case, the voltage 201 outgoing from these rectifying circuits should be direct and stabilized, with a prefixed value preferably comprised for instance between 50 V and 200 V, where the chosen voltage value depends on the utilization of the operating equipment.

Alternatively, for the same intended use of the equipment, the voltage can be different for different functions.

For instance, the feeding voltage can come from two feeders with two different voltage values for the scalpel bipolar function, or its single-polar function present on the same equipment.

Figure 2:
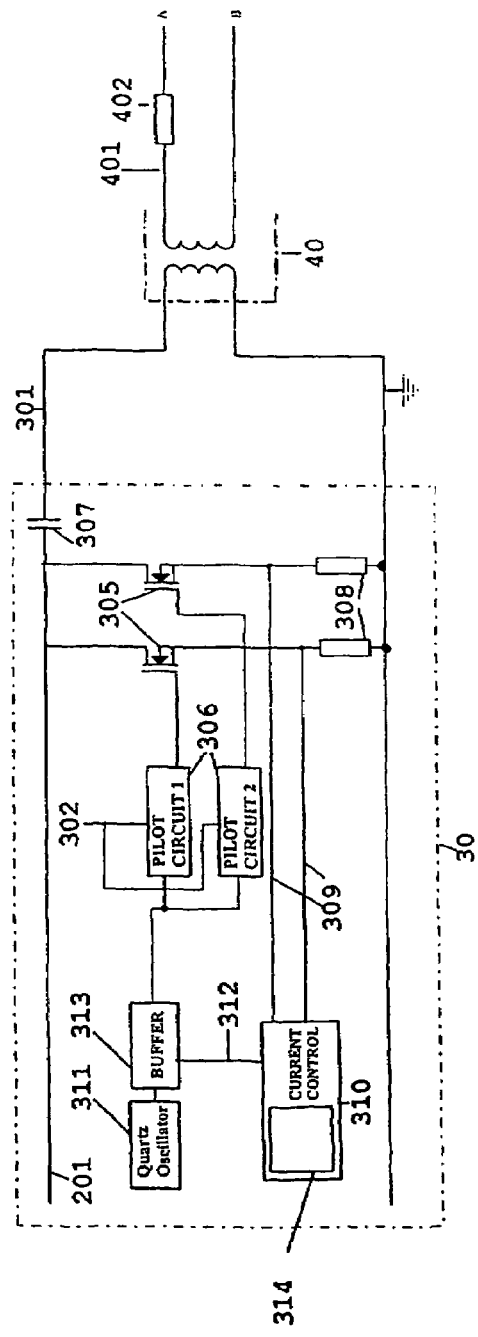
FIG. 2 is a detailed illustration of the radio frequency circuit of the electronic scalpel of FIG. 1.

This radio frequency circuit is better shown in FIG. 2.

The circuit in this example uses two electronic switches MOSFET.

However, if an electronic scalpel requires higher cutting powers, it is possible to use three or more MOSFET components.

Each MOSFET is controlled by a pilot circuit fed by the voltage supplied by a direct voltage stabilized power supply of known type not shown in the drawings, in which it is possible to regulate the output voltage, which can be also of switching type, to obtain a better efficiency.

The pilot circuit 306 is also regulated by a current control 310 comprising among others a microprocessor 314.

More particularly the radiofrequency circuit 30 provides that each MOSFET 305 acts as a switch breaking the direct current coming from the output voltage 201 of the rectifying circuit 20 and applied to the collector of each MOSFET.

Each pilot circuit 306 emits a unidirectional pulsating not alternated square wave 304 that drives the base of each MOSFET.

The frequency of the pilot circuit 306 is kept constant through a quartz oscillator 311 having an oscillation frequency of 4 MHz connected to a BUFFER 313.

The basic oscillation frequency of 4 MHz, and the higher frequencies too, can be also obtained by a circuit or a specific electronic device, like for instance a frequency synthesizer.

The control of MOSFET 305 occurs through a signal having an oscillation frequency equal to that of the quartz, or of the proper circuit or device, that in case of this example is 4 MHz.

The MOSFET 305 when closed interrupts the current on the leg 301 and when is open it lets the current to pass to the leg 301.

The width of the current wave form at 301 depends on the regulation of the signal 302 connected to the pilot circuit 306.

The regulation of the signal at 302, performed by a potentiometer 303, or for example by a regulator of touch screen type, allows to choose the width of the output wave so as to obtain the power intended for the manipulator 41 of the electronic scalpel according to the operation to be carried out.

The following table shows the maximum powers employed in some application fields, using the scalpel of the invention in cutting operations according to the surgical intervention fields.

TABLE 1

| FIELD | POWER OF SCALPEL |
|---|---|
| Plastic Surgery | Max 160 W |
| Maxillo Facial | Max 160 W |
| Dermatology | 50-120 W |
| ENT | Max 160 W |
| Gynaecology | Max 160 W |
| Neurosurgery | Max 90 W |
| Urology | Max 200 W |

From table 1 one can see that the maximum power employed can range from 50 Watts, for small dermatologic interventions, up to a maximum of 200 Watts, generally employed in urologic field.

To obtain a power adjustment method which is different from the one described in the example, providing for the power adjustment by the variation of the feeding voltage 302 of the drivers piloting the power MOSFETs gates, a still direct and stabilized (by AC/DC converter or by DC/DC converter), but variable for instance from 0 V to 200 V, voltage 201 can be used, while the voltage 302 is maintained steady.

Another possibility is that of using the direct and stabilized voltage 201, variable for instance from 0 V to 200 V, and the variable voltage 302 too to obtain in this case a power adjustment of mixed type.

The output signal of the radio frequency circuit therefore is a current pulsating wave 301 at the frequency of 4 MHz with a width regulated by the power regulator 303 which modifies the voltage 302.

As the output of the radio frequency circuit 30 is connected to the primary of the radio frequency transformer 40, a circulating current 301 is established passing through a resonant circuit at the frequency of 4 MHz, where the capacity and inductance of the resonant circuit are given by the eddy capacity of the MOSFET 305, the capacitor 307, of negligible reactance, but acting as lock of the direct component of a voltage 201 and the inductance of the primary circuit of the transformer 40, respectively.

According to the invention, the resonant circuit is of the wide pass-band type so as to let pass even if dampened, at least the second and the third harmonic of the carrier wave relative to the signal 301.

Preferably it is desired that the signal 301 has at least the second, the third and the fourth harmonic.

To obtain a wide pass-band resonant circuit in the embodiment of FIG. 2 a high frequency transformer was used, having a number of turns of the secondary circuit which is equal or greater than the number of turns of the primary circuit.

In this way, the dosage in decreasing and particular way of the harmonics greater than 4 MHz is obtained, also as a consequence of the kind of scalpel, or the device controlling it, which changes depending on the different surgical utilization fields.

As it is known, for a resonant circuit the resonance coefficient Q is given by the formula:

$$Q = \omega C_R R_E = 2\Pi f C_R R_E$$

where f is the resonance frequency, $C_R$ is the capacity of the resonant circuit, $R_E$ is the equivalent Resistance of the primary circuit when to the secondary circuit a load is applied consisting for instance of the patient's body to be operated with the electronic scalpel.

As the equivalent Resistance may be expressed by the formula:

$$R_E = R_C \left(\frac{N_1}{N_2}\right)^2$$

where $R_C$ is the load resistance and $N_1$ and $N_2$ is the number of turns of the primary and secondary respectively, one can see that the resonance factor Q may be expressed by the formula:

$$Q = 2\Pi f C_R R_C \left(\frac{N_1}{N_2}\right)^2$$

The formula points out that the resonance coefficient decreases when the number of the secondary turns increases relative to that of the primary turns.

The resonance coefficient may also be expressed with the formula:

$$Q = \frac{F_R}{B}$$

where $F_R$ is the resonance frequency and B is the pass-band.

In the case of the invention, when it is desired to widen the pass-band of 4 MHz to 8 MHz, 12 MHz and 16 MHz, in the resonant circuit a transformer is inserted with a suitable number of turns so that the resonance coefficient be lower than 1, preferably between 0.6 and 0.7.

Figure 3:
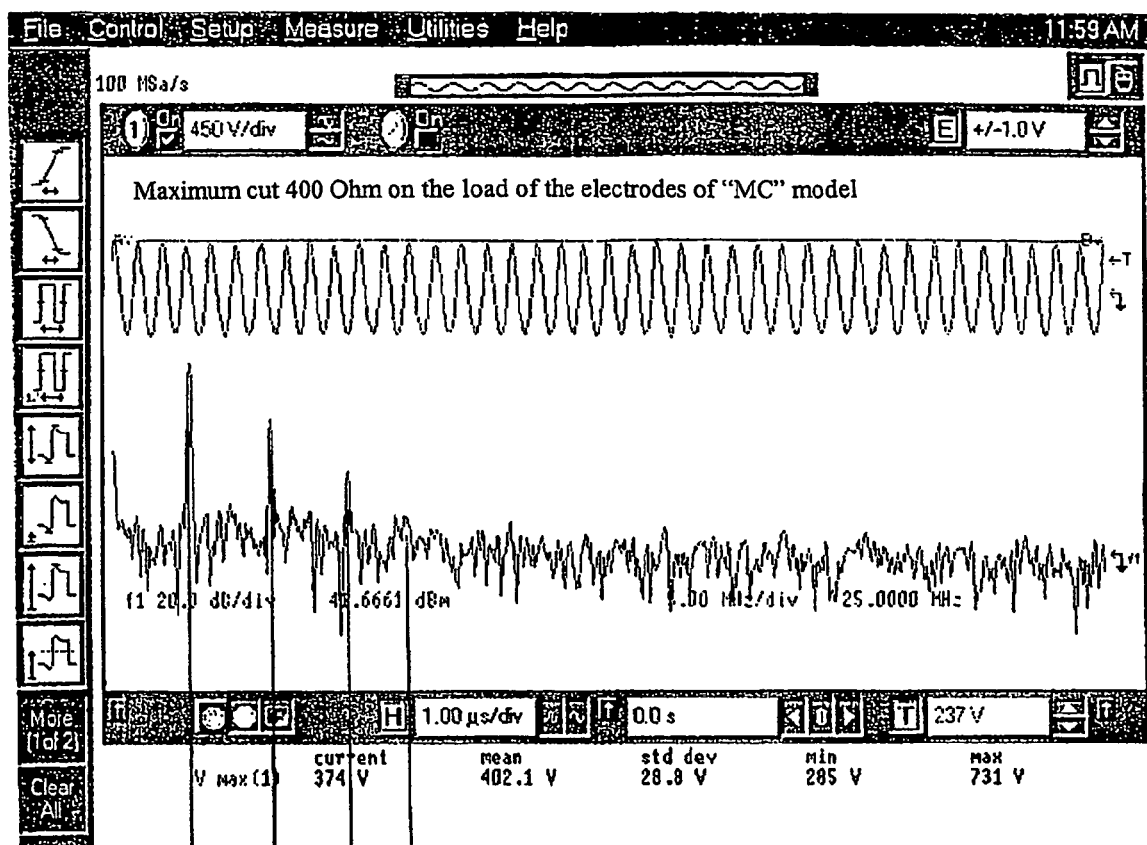
FIG. 3 shows the wave form of the power available at the manipulator of the electronic scalpel referred to the various frequencies.

With these characteristics of wide pass-band of the resonant circuit, the secondary current signal of the transformer at 401 takes the form shown in FIG. 3.

Checking the wave form of FIG. 3, one can see that at 4, 8, 12 and 16 MHz there are power peaks that are the interesting ones and are transferred to the scalpel manipulator with the above mentioned effects.

One can see that the current of signal 401, once the power regulator 303 is set, is controlled through a current control coming from a current sensor 308 arranged after the MOSFET 305.

The voltage signal 309 coming from the current sensor 308 drives the current control 310 providing to limit, through quick comparators controlled by the microprocessor 314, the maximum current 401 acting with the signal 312 on the pilot circuit of the MOSFET, or acting with the supplying voltage 201.

The current controller 310 can be a circuit or a specific electronic device, or the same microprocessor 314, which controls the entire system.

The current control can be also performed by the microprocessor 314, which controls the entire system, without employing fast comparators.

In case of low impedance, as the current would rise to very high values, in the circuit there is a current limiter consisting of the inductance 402 limiting the current to the manipulator and hindering the circuit to exceed the maximum admissible current value.

The electric circuit is closed through the patient's ohmic load between two electrodes which are the manipulator 41 and a plate electrode 42.

The plate 42 is preferably covered by a light insulating layer to avoid plate burns to the patient, which are typical of the electronic scalpel.

One can see that the electrode assembly constituted by manipulator 41 and plate 42 may also take the different form of pincers with bipolar operation.

With the adjustment method for regulating the electronic scalpel of the invention, the dosage of the energy transmitted to the cells cut by the scalpel is thus obtained, by the choice of a proper resonance frequency, of 4 MHz in the case of the invention, of the impulsive wave combined with the presence of harmonics.

Moreover, the dosage of the output power available at the manipulator of the electronic scalpel allows to provide for a power adapted to the nature of the intervention to be performed.

As a consequence of said kind of dosage, the advantages obtained are mainly a cold cut without tissue necrosis and with cheloids reduction, a sterile cut with fewer haemorrhages and fewer problems in the post-operating stage.

Furthermore, a very significant decrease of the pains felt by the patient in post-operating stage is obtained, and consequently a reduced stay time in hospital after surgery.

There is also the possibility to perform biopsies without any related necrosis.

It has to be noted that the surgery time is also reduced to a minimum.

It is possible to use as well the scalpel of the invention also on patients having pace-makers, because the frequencies chosen for said scalpel utilization do not interfere with pace-maker working.

As a consequence, a considerable cost reduction of the patients operations is obtained.

The invention claimed is:

1. A method for regulating the power supplied to an electronic scalpel having an electrode carried by a manipulator, said scalpel for cutting tissue, and having a rectifying circuit for supplying a rectified and direct voltage, and a radio frequency circuit for producing a current signal with substantially constant frequency feeding said manipulator through a radio frequency transformer, said radio frequency circuit having an electronic switch controlled by a circuit having an oscillator and a wide band pass resonant circuit operating at a resonant frequency, comprising the steps of:
generating a wave form having a selected resonant frequency and harmonics of at least first and second orders generated by the wide band pass resonant circuit, the wave form including a distorted sinusoidal voltage due to the presence of the harmonics;
applying the wave form to the manipulator for carrying power thereto; and
transferring to the tissue the manipulator power, such that, the power of the wave form at the resonant frequency and the harmonics, is substantially equal to the sum of energies required to break bonds of molecules forming the tissue.

2. An electronic scalpel for cutting tissue comprising:
a manipulator carrying an electrode to cut tissue and close a circuit;
a rectifying circuit for supplying a rectified voltage;
a radio frequency circuit including an electronic switch fed by said rectified voltage;
a pilot circuit for producing a generally square current wave of predetermined amplitude and frequency;
a resonant circuit feeding the manipulator for controlling the voltage, said radio frequency circuit producing an output current pulsating wave, the resonant circuit for circulating the output current pulsating wave comprising a wide pass-band circuit for transferring to the manipulator a distorted sinusoidal voltage including harmonics of a second and third order, and wherein said manipulator supplies to the tissue a wave form of selected frequencies resulting in an energy substantially equal to a sum of energies required to open molecular bonds the tissue.

3. The electronic scalpel according to claim 2 wherein the electronic switch has a parasitic capacity and including a transformer having a primary circuit with a selected inductance, wherein said resonant circuit comprises the parasitic capacity of said electronic switch and the inductance of the primary circuit of the transformer.

4. The electronic scalpel according to claim 2 including a regulator for controlling the pilot circuit, and wherein the wave form has a variable amplitude operably responsive to the pilot circuit.

5. The electronic scalpel according to claim 2 wherein the wave form has a variable amplitude at the manipulator in response to a modification of the rectified voltage , and a constant feeding the pilot circuit.

6. The electronic scalpel according to claim 2 wherein the wave form amplitude at the manipulator is variable in response the pilot circuit.

7. The electronic scalpel according to claim 2 wherein the radio frequency circuit emits a generally square wave at the frequency of about 4 MHz.

8. The electronic scalpel according to claim 7 wherein said resonant circuit transforms the square wave into a distorted sinusoidal wave.

9. The electronic scalpel according to claim 2 wherein said electronic switch comprises a MOSFET component.

10. The electronic scalpel according to claim 2 wherein the voltage at the manipulator has further harmonics of a fourth order.

11. The electronic scalpel according to claim 3 wherein the transformer has a number of secondary turns equal or greater than a number the primary turns, so that the resonant circuit has a resonance coefficient lower than 1.

12. The electronic scalpel according to claim 11 wherein the resonance coefficient of the resonant circuit is between about 0.6 and about 0.7.

13. The electronic scalpel according to claim 2 further including quartz oscillator for maintaining the frequency of the generally square current wave constant.

* * * * *

UNITED STATES PATENT AND TRADEMARK OFFICE
CERTIFICATE OF CORRECTION

PATENT NO. : 7,300,437 B2 Page 1 of 1
APPLICATION NO. : 10/559281
DATED : November 27, 2007
INVENTOR(S) : Pozzato It is certified that error appears in the above-identified patent and that said Letters Patent is hereby corrected as shown below:

On the Title Page (73) correct as shown:
ASSIGNEE: TELEA ELECTRONIC ENGINNERING SRL, (QUINTO, VICENTINO, IT)

Signed and Sealed this

Thirtieth Day of September, 2008

JON W. DUDAS
*Director of the United States Patent and Trademark Office*